US00PP37010P2

(12) United States Plant Patent
Kordes

(10) Patent No.: US PP37,010 P2
(45) Date of Patent: Oct. 14, 2025

(54) FLORIBUNDA ROSE PLANT NAMED 'KORfloci114'

(50) Latin Name: *Rosa hybrida*
Varietal Denomination: KORfloci114

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/217,038

(22) Filed: May 23, 2025

Related U.S. Application Data

(60) Provisional application No. 63/654,235, filed on May 31, 2024.

(51) Int. Cl.
*A01H 5/02* (2018.01)
*A01H 6/74* (2018.01)

(52) U.S. Cl.
USPC ..... Plt./145

(58) Field of Classification Search
USPC ..... Plt./101, 141, 145
See application file for complete search history.

(56) References Cited

U.S. PATENT DOCUMENTS

| | | | | |
|---|---|---|---|---|
| PP18,473 | P2 | 2/2008 | Carruth | |
| PP23,314 | P2 | 1/2013 | Kordes | |
| PP35,155 | P2 * | 5/2023 | Bedard | Plt./145 |

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of floribunda rose plant, referred to by its cultivar name, 'KORfloci114', is described. The new variety forms in abundance on a substantially continuous basis yellow-colored blossoms. The vegetation is vigorous, and the growth habit is compact and rounded. Additionally, the new variety is particularly well suited for growing as distinctive ornamentation in the landscape.

1 Drawing Sheet

CROSS REFERENCE TO RELATED APPLICATIONS

This application claims priority to U.S. Provisional Patent Application No. 63/654,235, which was filed on May 31, 2024, the contents of which are hereby incorporated by reference for all purposes.

Latin name of genus and species of plant claimed: *Rosa hybrida.*

Variety denomination: 'KORfloci114'.

STATEMENT REGARDING PRIOR DISCLOSURES BY THE INVENTOR

The first offer for sale of the new variety was June 2023, on the KORDES website. The first sale or offer for sale of the new variety was by the inventor or another who obtained the new variety directly or indirectly from the inventor. No plants of the new variety have been sold in this country or anywhere in the world, nor has any disclosure of the new plant been made, more than one year prior to the effective filing date of this application, and such sale or disclosure within one year was either derived directly or indirectly from the inventor.

BACKGROUND OF THE INVENTION

The new variety of floribunda rose plant of the present invention was created by controlled breeding in May 2010 in Sparrieshoop, Germany by artificial pollination wherein two parents were crossed which previously had been studied in the hope that they would contribute the desired characteristics. The female parent (i.e., the seed parent) was an unnamed breeder seedling (not patented). The male parent (i.e., the pollen parent) of the new variety was 'WEKvossutono' (U.S. Plant Pat. No. 18,473).

The parentage of the new variety can be summarized as follows:

unnamed breeder seedling x 'WEKvossutono'

The seeds resulting from the above pollination were sown and small plants were obtained which were physically and biologically different from each other. Selective study resulted in the identification of a single plant of the new variety.

The new variety has been found to undergo asexual propagation at Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) abundantly and substantially continuously forming yellow-colored blossoms,
(b) exhibiting a compact and rounded growth habit, and
(c) forming vigorous vegetation.

The new variety well meets the needs of the horticultural industry. It can be grown to advantage as distinctive ornamentation in parks, gardens, public areas, and residential landscapes. Accordingly, it is particularly well suited for growing in the landscape.

The new variety can be readily distinguished from its ancestors. More specifically, the new variety displays a larger flower size, more golden yellow flower color, and a higher petal count compared to the unnamed breeder seedling parent (i.e., the seed parent). Additionally, the new variety displays a more golden yellow flower color, a more compact growth habit, exhibits less petaloids, and better disease resistance compared to the 'WEKvossutono' variety (i.e., the pollen parent). Moreover, the new variety can be readily distinguished from non-parental related similar varieties. For example, the new variety displays a slightly smaller flower diameter, and a different shade of yellow flower color compared to the 'KORfloci52' (U.S. Plant Pat. No. 23,314).

The new variety has been named the 'KORfloci114' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a field on understock in Wasco, California, U.S.A. in June 2022.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a two-year-old specimen of the new variety, observed during May 2024, while growing on its own roots in a three-gallon container in Cochranville, Pennsylvania.

Botanical classification: *Rosa hybrida* cultivar 'KORfloci114'.

Commercial classification: Floribunda Rose.

Plant:

*Habit*.—Compact and rounded.

*Height*.—Approximately 91.0 cm on average from the top of the soil plane.

*Width*.—Approximately 91.0 cm on average.

Branches:

*Stem color*.—Old wood: Yellow-Green Group 144A. — young stems: Green Group 143A.

*Length*.—Main stems: approximately 60.0 cm on average. — secondary stems: approximately 31.0 cm on average.

*Diameter*.—Main stems: approximately 1.1 cm on average. — secondary stems: approximately 6.0 mm on average.

*Texture*.—Smooth.

*Prickles*.—Amount: moderate; 8 to 10 prickles per internode. — young prickles: length is approximately 5.0 mm on average; width is approximately 9.0 mm on average at point of attachment; and color is Yellow-Green Group N144A. — old prickles: length is approximately 8.0 mm on average; width is approximately 1.2 cm on average at point of attachment; and color is Greyed-Orange Group 165B.

Leaflets:

*Number*.—5 and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Glossy.

*Texture*.—Upper surface: smooth. — under surface: smooth.

*Venation pattern*.—Pinnate.

*Size*.—Terminal leaflet: length is approximately 5.0 cm on average; width is approximately 4.0 cm on average. — lower leaflets: length is approximately 4.0 cm on average; width is approximately 2.8 cm on average. — 5-Leaflet leaf. length is approximately 10.0 cm on average; width is approximately 8.5 cm on average.

Foliage:

*Young foliage*.—Upper surface color: Green Group 143C with indistinguishable venation. — under surface color: Yellow-Green Group 146D with indistinguishable venation.

*Old foliage*.—Upper surface color: Green Group 137A with indistinguishable venation. — under surface color: Yellow-Green Group 147B with indistinguishable venation.

*Petiole*.—Texture: upper surface is hispidulous; under surface is smooth. — length: approximately 2.0 cm on average. — width: approximately 1.0 mm on average. — upper surface color: Green Group 143B. — under surface color: Yellow-Green Group 144A.

*Rachis*.—Length: approximately 2.0 cm on average. — width: approximately 1.0 mm on average. — upper surface color: Green Group 143A. — under surface color: Yellow-Green Group 144A.

*Stipules*.—Length: approximately 1.5 cm on average. — width: approximately 6.0 mm on average. — margin: entire to erose. — upper surface color: Yellow-Green Group 144A. — lower surface color: Green Group 143A.

Inflorescence:

*Number of flowers*.—About 30 blooms on average on a plant at once.

*Number of blossoms per stem or in a cluster*.—Typically between 1 to 4 blooms per stem on average.

*Peduncle*.—Color: Yellow-Green Group 144B. — diameter: approximately 2.0 mm on average. — length: approximately 7.0 cm on average. — surface texture: hispidulous.

*Sepals*.—Number: 5. — upper surface color and texture: Yellow-Green Group 144D, covered in short pubescence. — under surface color and texture:

Yellow-Green Group 144A, puberulent. — size: length is approximately 2.0 cm on average; width is approximately 1.0 cm on average. — margin: entire with extensions on most sepals measuring approximately 3.0 mm in length and 1.0 mm in width on average. — apex: acute to aristate. — base: truncate as it joins the receptacle.

*Buds*.—Shape: ovoid. — size: length is approximately 2.0 cm on average; width is approximately 1.5 cm on average. — color (when opening): Yellow Group 7B.

*Flower*.—Form: double, cuplike. — profile: concave as it opens, and then outer petals are convex as the bloom ages and opens further. — diameter: approximately 6.0 cm on average. — height: approximately 4.0 cm on average. — duration: on the plant approximately 10 to 12 days. — petal color when first and fully opened: upper surface is Yellow-Orange Group 20B with a basal spot of Yellow Group 7A; under surface is Yellow Group 8B with a basal spot of Yellow Group 7A. — petal color at end of bloom: upper surface is Yellow-Orange Group 14D with a basal spot of Yellow Group 9B; under surface is Yellow-Orange Group 14D with a basal spot of Yellow Group 9B. — petals reflex one by one: yes.

*Fragrance*.—Slight sweet scent.

*Petal*.—Number: 30 to 35 on average. — drop: good. — length: typically 2.5 cm to 3.0 cm. — width: typically 2.0 cm to 3.0 cm. — overall shape: broadly obovate. — margin: entire with moderate undulation. — apex shape: rounded to slightly cuspidate. — base shape: cuneate. — texture: upper surface is smooth; under surface is smooth.

*Petaloids*.—Number: approximately 4 on average. — length: approximately 2.0 cm on average. — width: approximately 2.0 cm on average. — color: Yellow Group 11B, with a basal spot of Yellow Group 7A. — texture: upper surface is smooth; under surface is smooth. — margin: entire. — shape: spatulate. — apex: obovate. — base: truncate.

*Stamen*.—Number: approximately 183. — anthers: number is approximately 183; color is Yellow-Orange Group 22A; length is approximately 3.0 mm on average; and shape is oval. — filaments: length is approximately 5.0 mm on average and color is Yellow Group 7A.

*Pistils*.—Arrangement: separate and free. — number: approximately 164.— color: Yellow Group 4A. — style: length is approximately 5.0 mm on average and color is Yellow Group 4A. — stigma: diameter is approximately 1.0 mm on average; and shape is fan shaped.

*Receptacle*.—Diameter: approximately 9.0 mm on average. — depth: approximately 8.0 mm on average. — shape: urn shaped. — color: Yellow-Green Group 144A. — surface texture: smooth.

*Pollen*.—Amount: moderate. — color: Greyed-Orange Group 171A.

*Hips/seed*.—None observed.

Development:

*Vegetation*.—Vigorous.

*Blossoming*.—Abundant and substantially continuous from spring through frost; typically, in bloom outdoors from May to November in Southeastern Pennsylvania.

*Resistance to diseases*.—Very good resistance to powdery mildew (*Podosphaera pannosa*) and rust (*Phragmidium tuberculatum*).

*Hardiness*.—Hardy to USDA Zone 6.

The new 'KORfloci114' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant named 'KORfloci114' characterized by the following combination of characteristics:

(a) abundantly and substantially continuously forming yellow-colored blossoms, (b) exhibiting compact and rounded growth habit, and (c) forming vigorous vegetation;

substantially as herein shown and described.

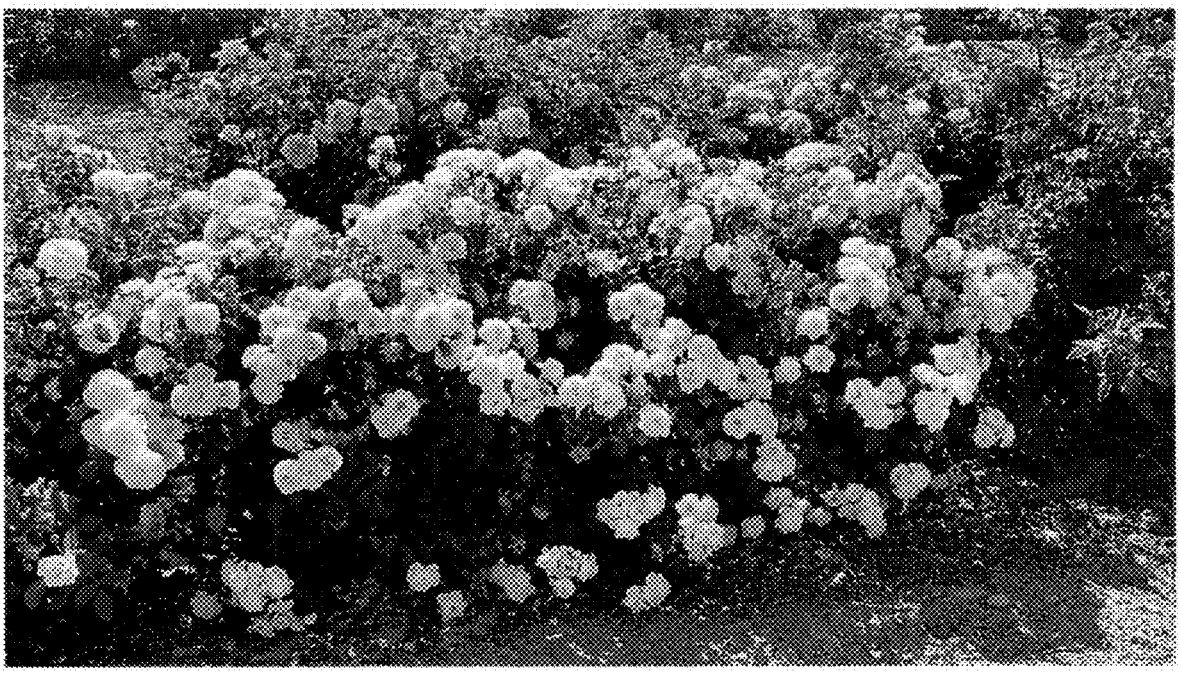

* * * * *